US012066654B2

(12) United States Patent
Novak, III et al.

(10) Patent No.: US 12,066,654 B2
(45) Date of Patent: Aug. 20, 2024

(54) CHARGING CONTROL FOR AN AEROSOL DELIVERY DEVICE

(71) Applicant: RAI Strategic Holdings, Inc., Winston-Salem, NC (US)

(72) Inventors: Charles Jacob Novak, III, Winston-Salem, NC (US); Sean A. Daugherty, Yadkinville, NC (US); Jason L. Wood, Lexington, NC (US); Michael Ryan Galloway, Winston-Salem, NC (US); Mark Frisbee, Raleigh, NC (US); Raymond Charles Henry, Jr., Cary, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 868 days.

(21) Appl. No.: 16/537,784

(22) Filed: Aug. 12, 2019

(65) Prior Publication Data

US 2020/0154779 A1   May 21, 2020

Related U.S. Application Data

(60) Provisional application No. 62/769,296, filed on Nov. 19, 2018.

(51) Int. Cl.
*A24F 40/90* (2020.01)
*A24F 40/50* (2020.01)
(Continued)

(52) U.S. Cl.
CPC .............. *G02B 6/009* (2013.01); *A24F 40/50* (2020.01); *A24F 40/90* (2020.01); *A61M 11/041* (2013.01);
(Continued)

(58) Field of Classification Search
CPC ................... A24F 40/50; A24F 40/90
(Continued)

(56) References Cited

U.S. PATENT DOCUMENTS 2,057,353 A   10/1936  Whittemore, Jr.
2,104,266 A   1/1938   McCormick
(Continued)

FOREIGN PATENT DOCUMENTS

CA   3048772 A1   8/2018
CN   1541577      11/2004
(Continued)

OTHER PUBLICATIONS

International Search Report from corresponding International Application No. PCT/IB2019/059455, mailed Feb. 7, 2020.
(Continued)

*Primary Examiner* — Russell E Sparks
(74) *Attorney, Agent, or Firm* — Womble Bond Dickinson (US) LLP

(57) ABSTRACT

The present disclosure provides an aerosol delivery device. The aerosol delivery device comprises one or more rechargeable batteries, charging circuitry including an electrical connector configured to interconnect the one or more rechargeable batteries with a power supply, and a sensor configured to detect an action of using the aerosol delivery device by a user and output a signal. The aerosol delivery device also comprises a microprocessor coupled to the charging circuitry and the sensor, the microprocessor, in response to receiving the signal from the sensor, is configured to control the aerosol delivery device to allow vaping or puffing by a user while the aerosol delivery device is connected to a charger.

13 Claims, 11 Drawing Sheets

(51) Int. Cl.
  *A61M 11/04* (2006.01)
  *F21V 8/00* (2006.01)
  *F21V 23/00* (2015.01)
  *G05B 19/042* (2006.01)
  *H02J 7/00* (2006.01)
  *F21Y 115/10* (2016.01)

(52) U.S. Cl.
  CPC ......... *A61M 11/042* (2014.02); *F21V 23/005* (2013.01); *G02B 6/0083* (2013.01); *G05B 19/042* (2013.01); *H02J 7/00* (2013.01); *H02J 7/0063* (2013.01); *H02J 7/007* (2013.01); *A61M 2205/3331* (2013.01); *A61M 2205/3576* (2013.01); *A61M 2205/50* (2013.01); *A61M 2205/587* (2013.01); *F21Y 2115/10* (2016.08); *G05B 2219/2639* (2013.01)

(58) Field of Classification Search
  USPC .......................................................... 131/329
  See application file for complete search history.

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,043,560 A | 8/1991 | Masreliez | |
| 5,060,671 A | 10/1991 | Counts et al. | |
| 5,093,894 A | 3/1992 | Deevi et al. | |
| 5,894,841 A | 4/1999 | Voges | |
| 6,125,853 A | 10/2000 | Susa et al. | |
| 6,155,268 A | 12/2000 | Takeuchi | |
| 6,683,778 B2* | 1/2004 | Yugou | B60L 3/0023 |
| | | | 361/179 |
| 6,977,513 B2* | 12/2005 | Matsunaga | H02H 7/18 |
| | | | 320/134 |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 8,528,569 B1 | 9/2013 | Newton | |
| 8,833,364 B2 | 9/2014 | Buchberger | |
| 9,220,304 B2 | 12/2015 | Greim | |
| 9,462,831 B2 | 10/2016 | Liu | |
| 9,655,383 B2* | 5/2017 | Holzherr | A24F 40/95 |
| 9,814,262 B2 | 11/2017 | Peleg et al. | |
| 9,814,263 B2 | 11/2017 | Cochand et al. | |
| 9,877,508 B2 | 1/2018 | Kane | |
| 9,949,507 B2 | 4/2018 | Flick | |
| 10,015,990 B2 | 7/2018 | Mironov | |
| 10,028,537 B1 | 7/2018 | Hawes et al. | |
| 10,058,125 B2 | 8/2018 | Worm et al. | |
| 10,080,851 B2 | 9/2018 | Davidson et al. | |
| 10,085,481 B2 | 10/2018 | Verleur et al. | |
| 10,092,037 B2 | 10/2018 | Tucker et al. | |
| 10,104,913 B2 | 10/2018 | Lau et al. | |
| 10,117,463 B2 | 11/2018 | Thomas | |
| 10,117,467 B2 | 11/2018 | Hawes et al. | |
| 10,461,807 B2* | 10/2019 | Bernauer | H05B 1/0244 |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0151717 A1 | 6/2009 | Bowen et al. | |
| 2009/0188490 A1 | 7/2009 | Hon | |
| 2009/0272379 A1 | 11/2009 | Thorens et al. | |
| 2009/0320863 A1 | 12/2009 | Fernando et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2012/0312313 A1* | 12/2012 | Frija | A24F 40/42 |
| | | | 131/329 |
| 2013/0037041 A1 | 2/2013 | Worm et al. | |
| 2013/0042865 A1 | 2/2013 | Monsees et al. | |
| 2013/0104916 A1 | 5/2013 | Bellinger et al. | |
| 2013/0306084 A1 | 11/2013 | Flick | |
| 2013/0319435 A1 | 12/2013 | Flick | |
| 2014/0000638 A1 | 1/2014 | Sebastian et al. | |
| 2014/0096781 A1 | 4/2014 | Sears et al. | |
| 2014/0096782 A1 | 4/2014 | Ampolini et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0278250 A1 | 9/2014 | Smith et al. | |
| 2014/0366898 A1 | 12/2014 | Monsees et al. | |
| 2015/0020831 A1 | 1/2015 | Weigensberg et al. | |
| 2015/0020832 A1 | 1/2015 | Greim et al. | |
| 2015/0150308 A1 | 6/2015 | Monsees et al. | |
| 2015/0164142 A1 | 6/2015 | Li et al. | |
| 2015/0189916 A1 | 7/2015 | Wu | |
| 2015/0208729 A1 | 7/2015 | Monsees et al. | |
| 2015/0313287 A1 | 11/2015 | Verleur et al. | |
| 2015/0359263 A1 | 12/2015 | Bellinger | |
| 2016/0157524 A1 | 6/2016 | Bowen et al. | |
| 2016/0242466 A1 | 8/2016 | Lord et al. | |
| 2016/0374397 A1 | 12/2016 | Jordan et al. | |
| 2017/0027226 A1 | 2/2017 | Mironov et al. | |
| 2017/0071256 A1 | 3/2017 | Verleur et al. | |
| 2017/0095005 A1 | 4/2017 | Monsees et al. | |
| 2017/0135404 A1 | 5/2017 | Reevell | |
| 2017/0135405 A1 | 5/2017 | Reevell | |
| 2017/0135406 A1 | 5/2017 | Reevell | |
| 2017/0143042 A1 | 5/2017 | Batista et al. | |
| 2017/0215485 A1 | 8/2017 | Zitzke | |
| 2017/0231281 A1 | 8/2017 | Hatton et al. | |
| 2017/0231282 A1 | 8/2017 | Hatton et al. | |
| 2017/0251728 A1 | 9/2017 | Peleg et al. | |
| 2017/0273736 A1 | 9/2017 | Paamand | |
| 2017/0325289 A1 | 11/2017 | Liu | |
| 2017/0340011 A1 | 11/2017 | Batista | |
| 2017/0340012 A1 | 11/2017 | Mironov et al. | |
| 2017/0347707 A1 | 12/2017 | Xiang | |
| 2017/0347711 A1 | 12/2017 | Litten et al. | |
| 2017/0347712 A1 | 12/2017 | Singh | |
| 2017/0367410 A1 | 12/2017 | Hon | |
| 2018/0000157 A1 | 1/2018 | Batista et al. | |
| 2018/0000160 A1 | 1/2018 | Taschner et al. | |
| 2018/0014575 A1 | 1/2018 | Fursa | |
| 2018/0020727 A1 | 1/2018 | Hoffman et al. | |
| 2018/0020731 A1 | 1/2018 | Rasmussen et al. | |
| 2018/0020736 A1 | 1/2018 | Silvestrini | |
| 2018/0027878 A1 | 2/2018 | Dendy et al. | |
| 2018/0035717 A1 | 2/2018 | Batista | |
| 2018/0042306 A1 | 2/2018 | Atkins et al. | |
| 2018/0043114 A1 | 2/2018 | Bowen et al. | |
| 2018/0070648 A1 | 3/2018 | Monsees et al. | |
| 2018/0077967 A1 | 3/2018 | Hatton et al. | |
| 2018/0084608 A1 | 3/2018 | Bernauer et al. | |
| 2018/0084831 A1 | 3/2018 | Mironov | |
| 2018/0103685 A1 | 4/2018 | Yener | |
| 2018/0132525 A1 | 5/2018 | Patil et al. | |
| 2018/0140010 A1 | 5/2018 | Sur et al. | |
| 2018/0140019 A1 | 5/2018 | Guo et al. | |
| 2018/0177230 A1 | 6/2018 | Hawes et al. | |
| 2018/0206557 A1 | 7/2018 | Peleg et al. | |
| 2018/0213844 A1 | 8/2018 | Sur et al. | |
| 2018/0213850 A1 | 8/2018 | Brinkley et al. | |
| 2018/0235282 A1 | 8/2018 | Gao et al. | |
| 2018/0242643 A1 | 8/2018 | Silvestrini et al. | |
| 2018/0280637 A1 | 10/2018 | Mayle et al. | |
| 2018/0295888 A1 | 10/2018 | Newcomb et al. | |
| 2018/0296777 A1 | 10/2018 | Terry et al. | |
| 2018/0303161 A1 | 10/2018 | Bilat | |

(56) References Cited

U.S. PATENT DOCUMENTS

2018/0325182 A1 11/2018 Zitzke et al.
2019/0217028 A1* 7/2019 Nakano ............... A24F 40/485

FOREIGN PATENT DOCUMENTS

| | | |
|---|---|---|
| CN | 2719043 | 8/2005 |
| CN | 201379072 | 1/2010 |
| CN | 105307524 A | 2/2016 |
| CN | 105611847 A | 5/2016 |
| CN | 107708456 A | 2/2018 |
| CN | 108135268 A | 6/2018 |
| CN | 110446435 A | 11/2019 |
| DE | 102007011120 A1 | 9/2008 |
| EP | 1 618 803 | 1/2006 |
| GB | 2542270 A | 3/2017 |
| WO | WO 2004/080216 | 9/2004 |
| WO | WO 2005/099494 | 10/2005 |
| WO | WO 2007/131449 | 11/2007 |
| WO | WO 2016/026811 | 2/2016 |
| WO | WO 2017/051006 | 9/2016 |
| WO | WO 2016200382 | 12/2016 |
| WO | WO 2016/207442 | 5/2017 |
| WO | WO 2017/147560 | 8/2017 |
| WO | WO 2018100495 | 6/2018 |
| WO | 2018/163261 A1 | 9/2018 |
| WO | WO 2018/167166 | 9/2018 |
| WO | 2018188863 A1 | 10/2018 |
| WO | WO 2018/202732 | 11/2018 |

OTHER PUBLICATIONS

Office Action issued Dec. 19, 2023, in corresponding Chinese Application No. 201980089574.1.

Decision of Rejection issued Apr. 9, 2024, in corresponding Japanese Application No. 2021-527176.

* cited by examiner

CHARGING CONTROL FOR AN AEROSOL DELIVERY DEVICE

CROSS-REFERENCE TO RELATED APPLICATIONS

The present application claims priority to U.S. Provisional Patent Application No. 62/769,296, filed Nov. 19, 2018, which is incorporated herein by reference.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes).

The smoking articles may be configured to heat an aerosol precursor, which may incorporate materials that may be made or derived from tobacco or otherwise incorporate tobacco, the precursor being capable of forming an inhalable substance for human consumption.

BACKGROUND

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

It would be desirable to allow vaping by a user while the aerosol delivery device is connected to the charger. Also, in some instances, the aerosol delivery device may stop allowing puffs due to a low battery condition. Thus, it would be desirable to allow puffs to occur as soon as the aerosol delivery device (with depleted battery) is connected to the charger, even though the battery level has not returned yet.

SUMMARY OF THE DISCLOSURE

The present disclosure relates to aerosol delivery devices, methods of forming such devices, and elements of such devices. The disclosure particularly can relate to an aerosol delivery system configured for allowing vaping by a user while the aerosol delivery device is coupled to an external power source for charging. The present disclosure includes, without limitation, the following example implementations.

Some example implementations provide an aerosol delivery device comprising: a rechargeable battery or multiple batteries; charging circuitry including an electrical connector configured to interconnect the rechargeable battery/batteries with a power supply; a sensor configured to detect an action of using the aerosol delivery device by a user and output a signal; and a microprocessor coupled to the charging circuitry and the sensor, the microprocessor, in response to receiving the signal from the sensor, being configured to: determine a state indicating an occurrence of a passage of electrical current from the power supply to the rechargeable battery/batteries through the electrical connector; discontinue the passage of the electrical current from the power supply to the rechargeable battery/batteries through the electrical connector; and activate the aerosol delivery device so that power is delivered from the rechargeable battery/batteries to a further element of the aerosol delivery device to provide an output in response to the action of using the aerosol delivery device by the user while the electrical connector is connected to the power supply.

In some example implementations of the aerosol delivery device of any preceding example implementation, or any combination of any preceding example implementations, the microprocessor being configured to discontinue the passage of the electrical current includes being configured to discontinue the passage of the electrical current using a switch circuit between the electrical connector and the rechargeable battery/batteries.

In some example implementations of the aerosol delivery device of any preceding example implementation, or any combination of any preceding example implementations, the switch circuit includes a pair of metal-oxide-semiconductor field-effect transistor (MOSFET) switches respectively coupled to a positive electrical connection and a negative electrical connection of the electrical connector, and the microprocessor being configured to discontinue the passage of the electrical current includes being configured to disconnect both the positive and negative electrical connections from the rechargeable battery/batteries using the switch circuit.

In some example implementations of the aerosol delivery device of any preceding example implementation, or any combination of any preceding example implementations, the switch circuit includes a pair of opto-isolator relays respectively coupled to a positive electrical connection and a negative electrical connection of the electrical connector, and the microprocessor being configured to discontinue the passage of the electrical current includes being configured to disconnect both the positive and negative electrical connections from the rechargeable battery/batteries using the switch circuit.

In some example implementations of the aerosol delivery device of any preceding example implementation, or any combination of any preceding example implementations, the switch circuit is coupled to one or both of a positive electrical connection and a negative electrical connection of the electrical connector, and the microprocessor being configured to discontinue the passage of the electrical current includes being configured to disconnect only one of the positive and negative electrical connections from the rechargeable battery/batteries using the switch circuit.

In some example implementations of the aerosol delivery device of any preceding example implementation, or any combination of any preceding example implementations, the switch circuit includes a MOSFET switch integrated with the charging circuitry and another switch external to the charging circuitry, and the microprocessor being configured to discontinue the passage of the electrical current includes being configured to disconnect the electrical connector from the rechargeable battery/batteries using the switch circuit.

In some example implementations of the aerosol delivery device of any preceding example implementation, or any combination of any preceding example implementations, in response to detecting a completion of the action by the sensor, the microprocessor is further configured to: determine that the electrical connector is connected to the power supply; and reconnect the electrical connector to the rechargeable battery and thereby reconnect the power supply to the rechargeable battery/batteries to charge the rechargeable battery/batteries.

In some example implementations of the aerosol delivery device of any preceding example implementation, or any combination of any preceding example implementations, the action includes a puff action by the user.

In some example implementations of the aerosol delivery device of any preceding example implementation, or any combination of any preceding example implementations, the further element includes a heating element configured to heat and thereby vaporize components of an aerosol precursor composition contained within a housing of the aerosol delivery device such that the output in response to the action of using the aerosol delivery device is formation of an aerosol.

In some example implementations of the aerosol delivery device of any preceding example implementation, or any combination of any preceding example implementations, the aerosol precursor composition is a liquid, solid or semi-solid.

In some example implementations of the aerosol delivery device of any preceding example implementation, or any combination of any preceding example implementations, the microprocessor is further configured to perform a comparison between a voltage of the battery/batteries and a voltage threshold of the battery/batteries to determine whether the voltage of the battery/batteries is higher than the voltage threshold; and wherein the microprocessor being configured to activate the aerosol delivery device includes being configured to activate the aerosol delivery device based on the comparison.

In some example implementations of the aerosol delivery device of any preceding example implementation, or any combination of any preceding example implementations, the microprocessor being configured to perform the comparison includes being configured to: alter the voltage threshold of the battery/batteries from a first value to a second value that is lower than the first value; and determine that the voltage of the battery/batteries is lower than the first value and higher than the second value.

Some example implementations provide an aerosol delivery device comprising: a rechargeable battery; charging circuitry including an electrical connector configured to interconnect the rechargeable battery/batteries with a power supply; a sensor configured to detect an action of using the aerosol delivery device by a user and output a signal; and a microprocessor coupled to the charging circuitry and the sensor, the microprocessor, in response to receiving the signal from the sensor, being configured to: determine that the electrical connector is connected to the power supply; perform a comparison between a voltage of the battery/batteries and a voltage threshold of the battery/batteries to determine whether the voltage of the battery/batteries is higher than the voltage threshold; and based on the comparison, determine whether to allow an activation of the aerosol delivery device so that power is delivered to a further element of the aerosol delivery device to provide an output in response to the action of using the aerosol delivery device by the user while the electrical connector is connected to the power supply.

In some example implementations of the aerosol delivery device of any preceding example implementation, or any combination of any preceding example implementations, the microprocessor being configured to perform the comparison includes being configured to: alter the voltage threshold of the battery/batteries from a first value to a second value that is lower than the first value; and determine that the voltage of the battery/batteries is lower than the first value and higher than the second value; and wherein the microprocessor being configured to determine whether to allow the activation of the aerosol delivery device includes being configured to allow the activation of the aerosol delivery device to carry out the action.

In some example implementations of the aerosol delivery device of any preceding example implementation, or any combination of any preceding example implementations, the first value is 3.5 volts and the second value is 3.3 volts or 3.4 volts.

In some example implementations of the aerosol delivery device of any preceding example implementation, or any combination of any preceding example implementations, the microprocessor being configured to perform the comparison includes being configured to determine that the voltage of the battery/batteries is lower than the second value; and wherein the microprocessor being configured to determine whether to allow the activation of the aerosol delivery device includes being configured to disallow the activation of the aerosol delivery device to carry out the action.

In some example implementations of the aerosol delivery device of any preceding example implementation, or any combination of any preceding example implementations, the action includes a puff action by the user.

In some example implementations of the aerosol delivery device of any preceding example implementation, or any combination of any preceding example implementations, the further element includes a heating element configured to heat and thereby vaporize components of an aerosol precursor composition contained within a housing of the aerosol delivery device.

In some example implementations of the aerosol delivery device of any preceding example implementation, or any combination of any preceding example implementations, the aerosol precursor composition is a liquid, solid or semi-solid.

In some example implementations of the aerosol delivery device of any preceding example implementation, or any combination of any preceding example implementations, in response to receiving the signal from the sensor, the microprocessor is further configured to:

determine a state indicating an occurrence of a passage of electrical current from the power supply to the rechargeable battery/batteries through the electrical connector; and discontinue the passage of the electrical current from the power supply to the rechargeable battery/batteries through the electrical connector.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1:
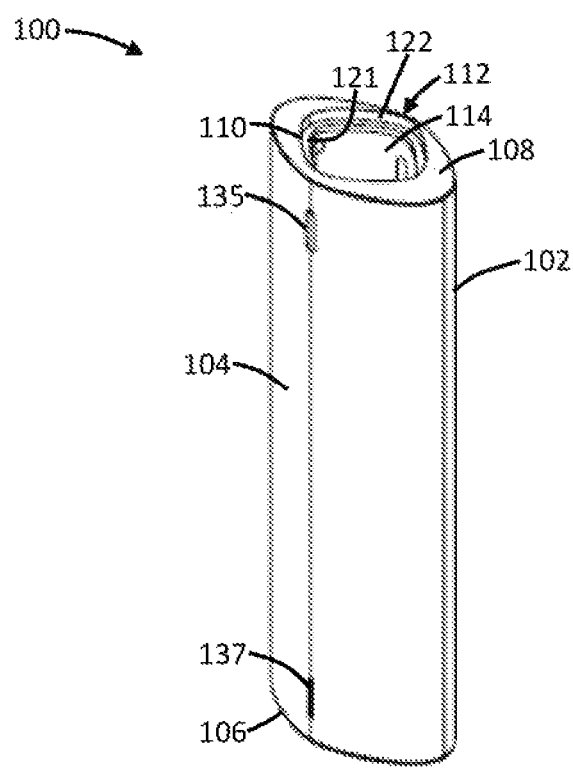
Figure 2:
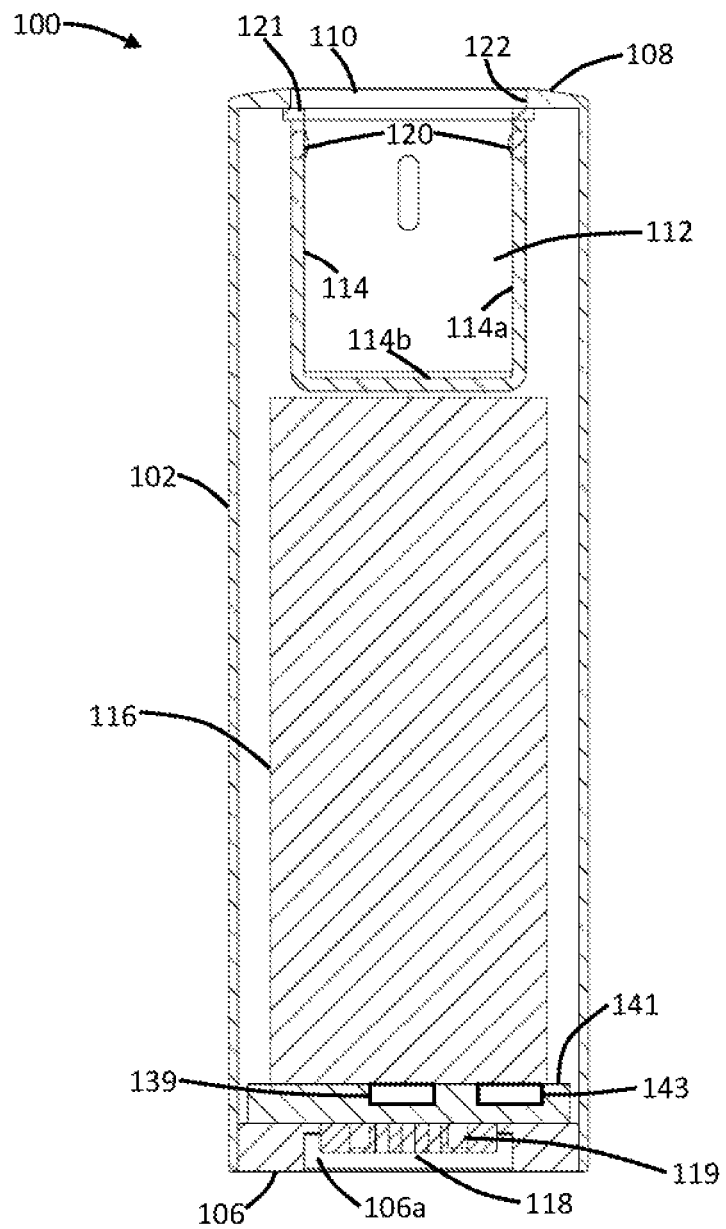
Figure 3:
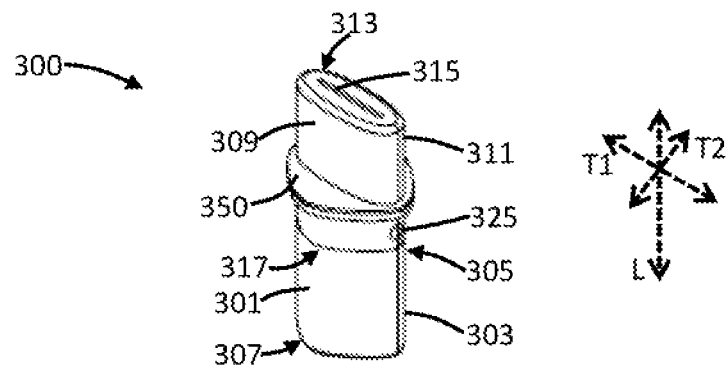
Figure 4:
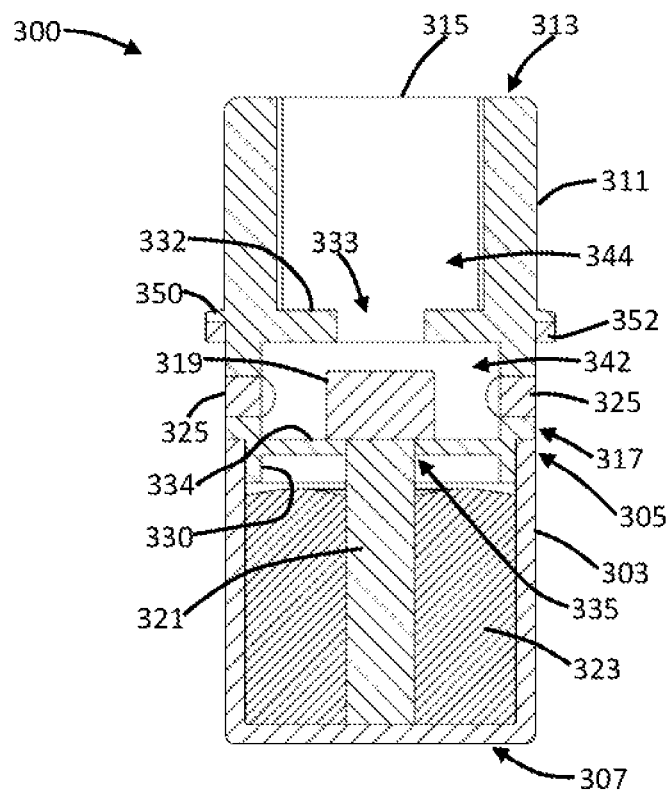
Figure 5A:
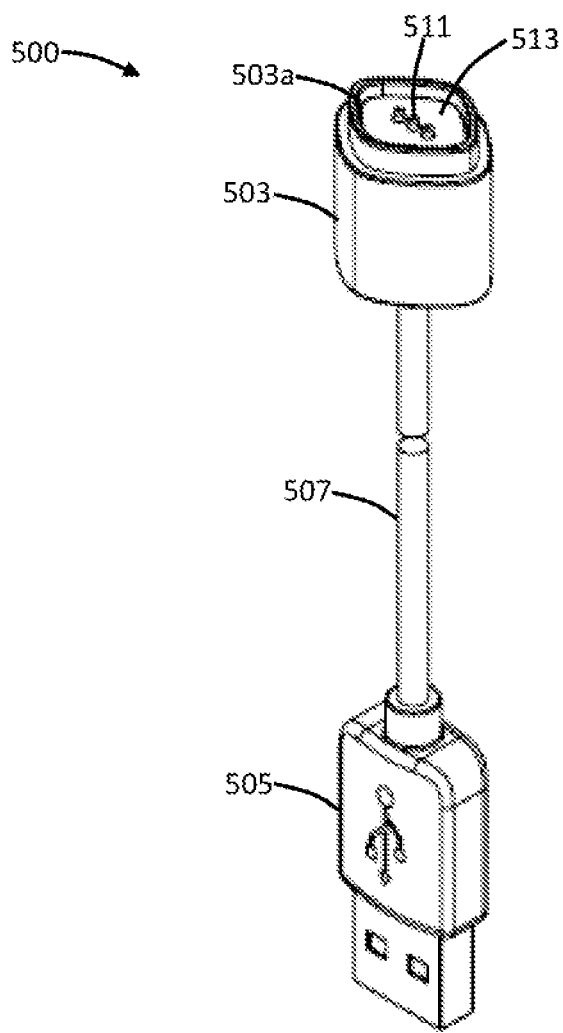
Figure 5B:
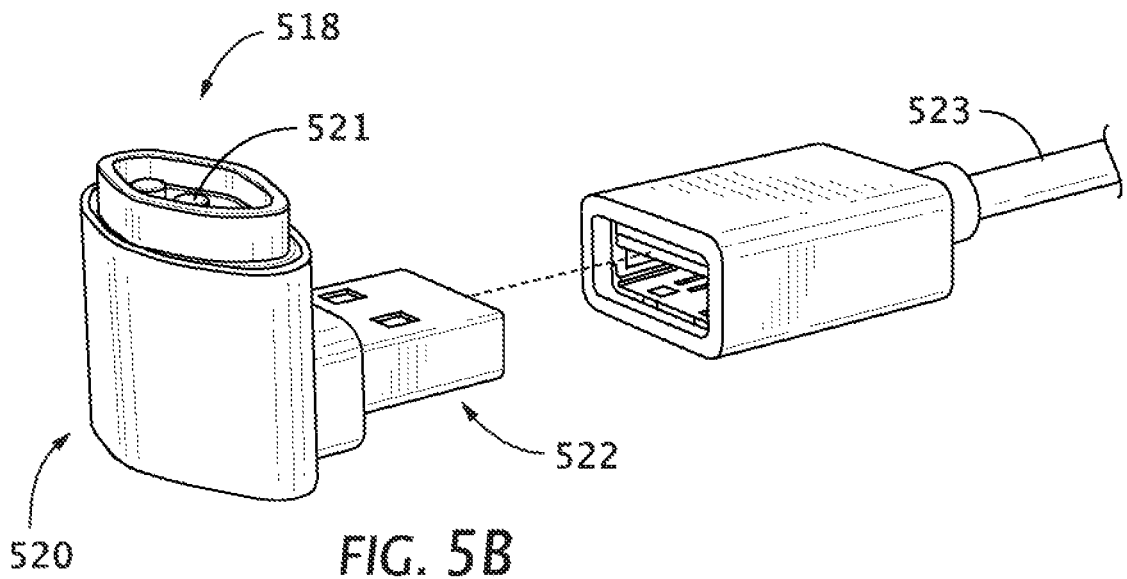
Figure 5C:
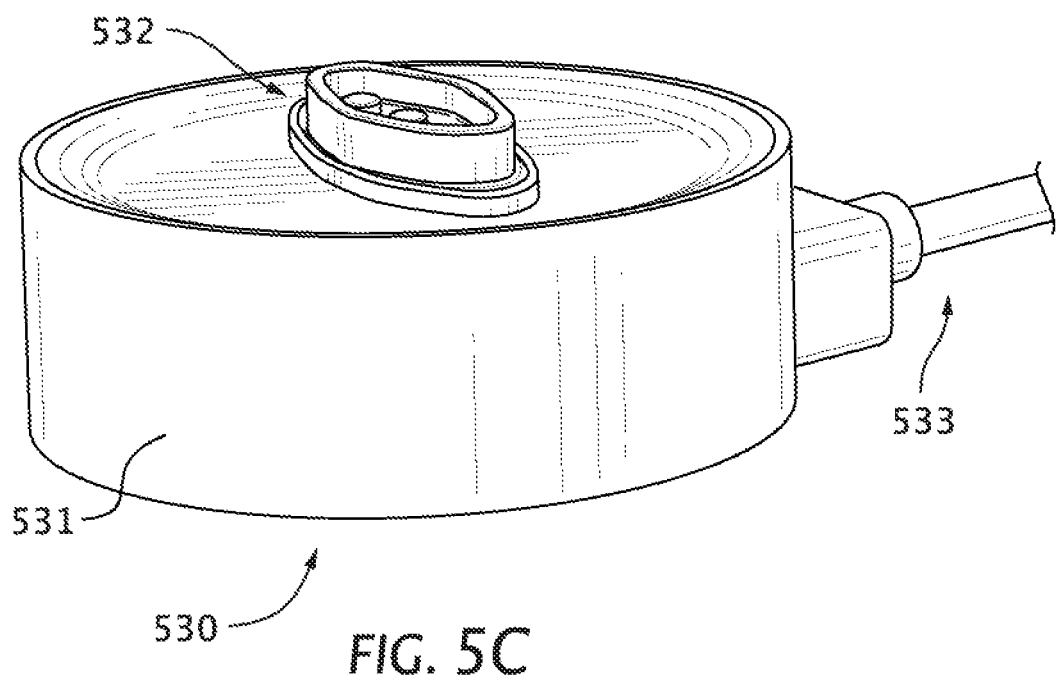
Figure 6:
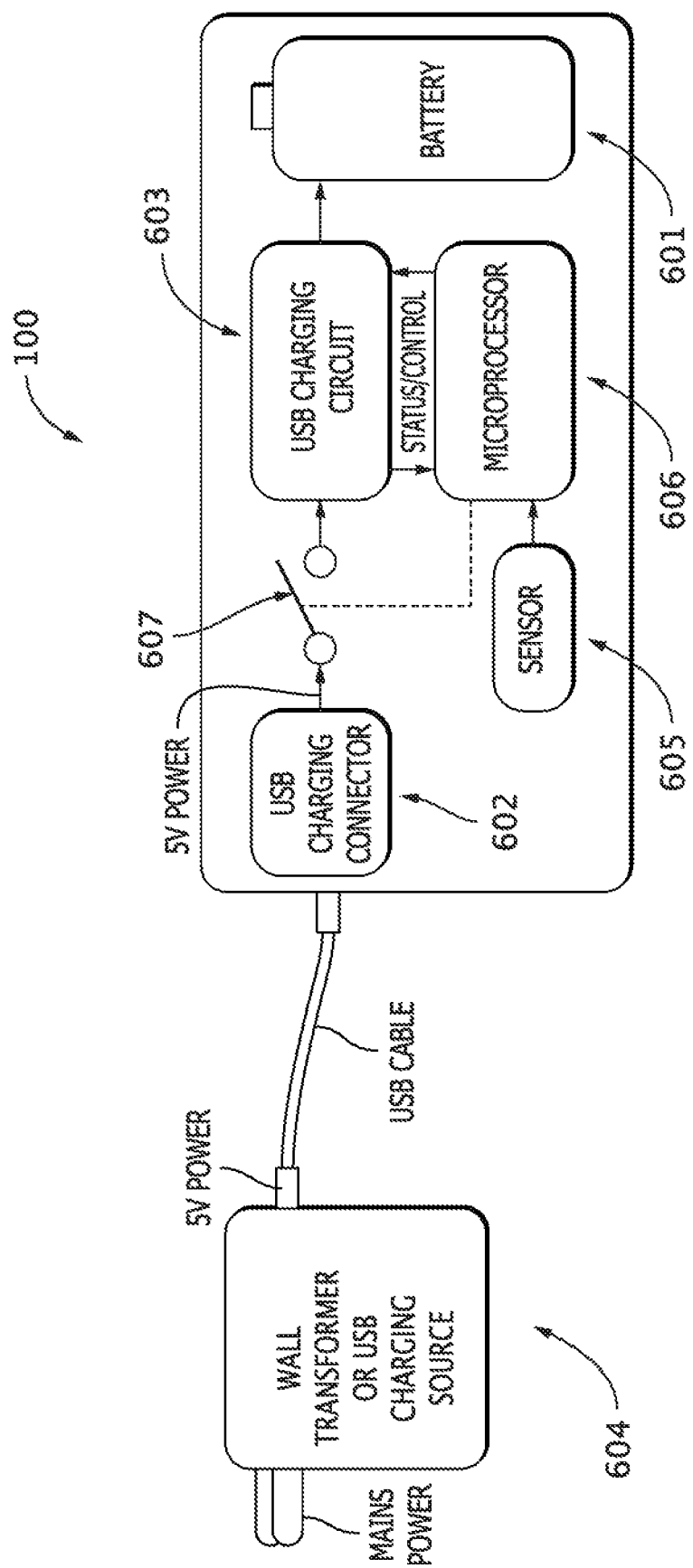
Figure 7A:
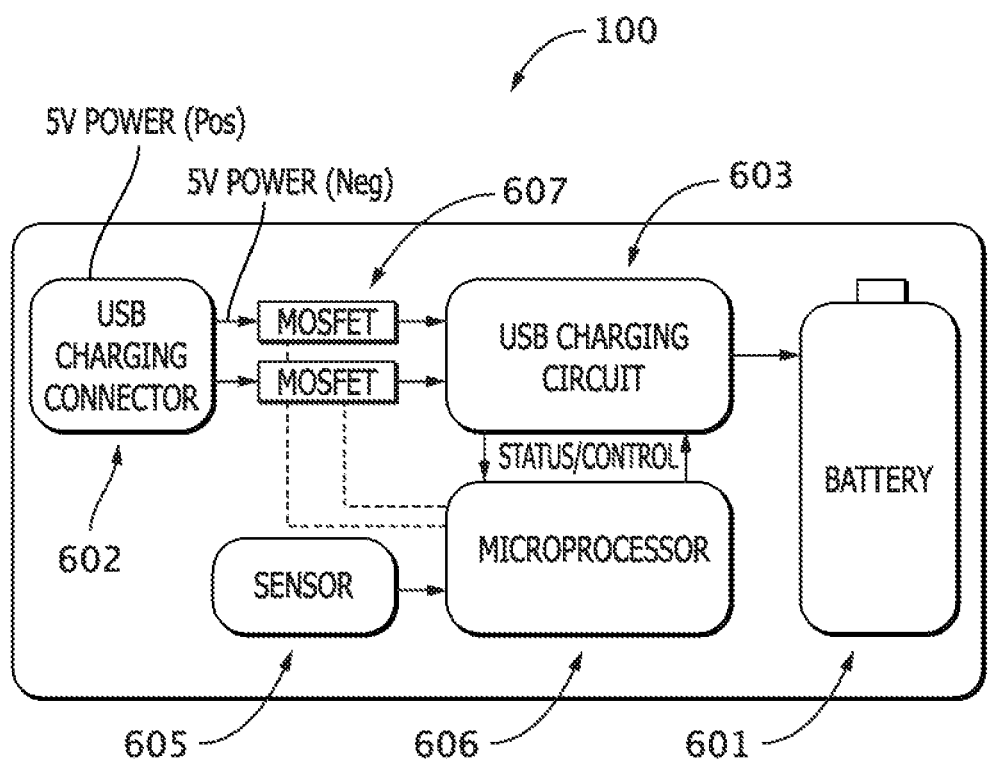
Figure 7B:
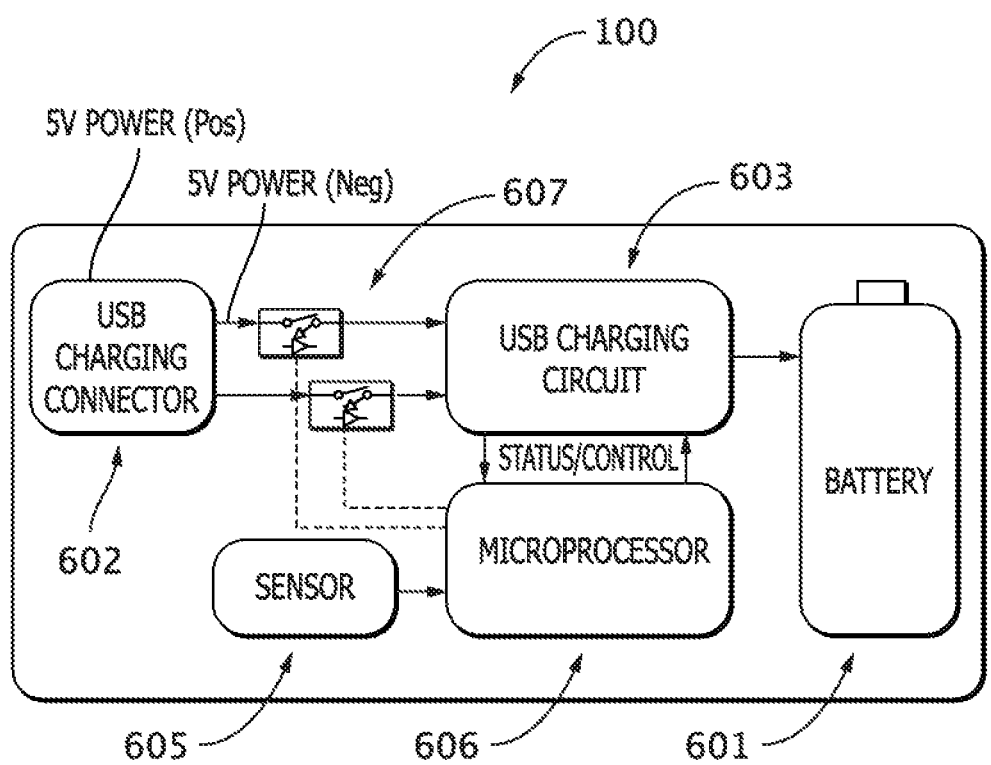
Figure 7C:
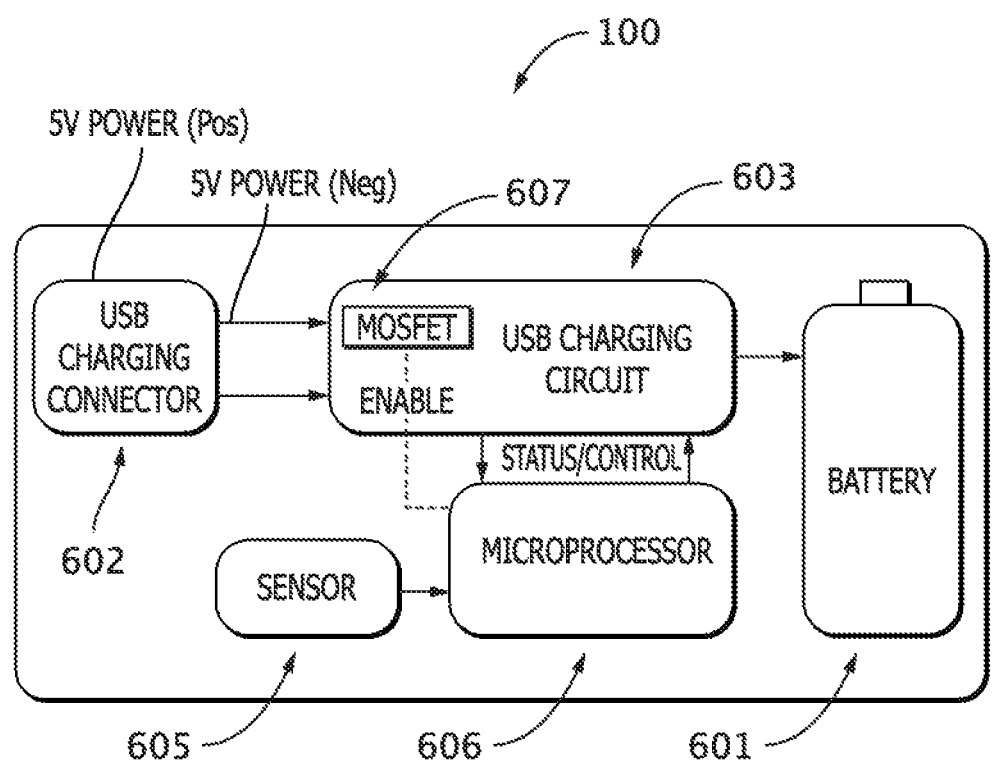
Figure 8:
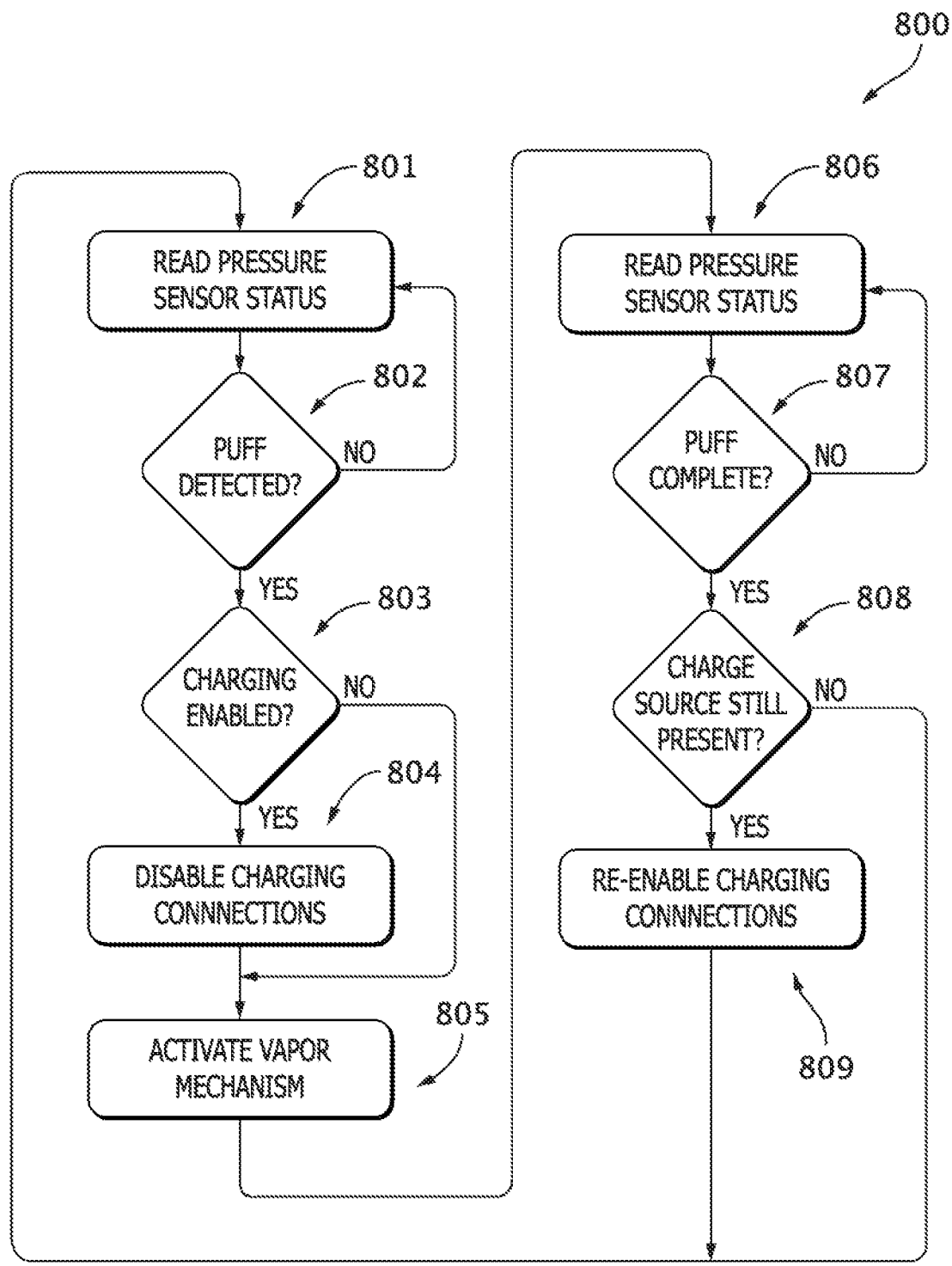
Figure 9:
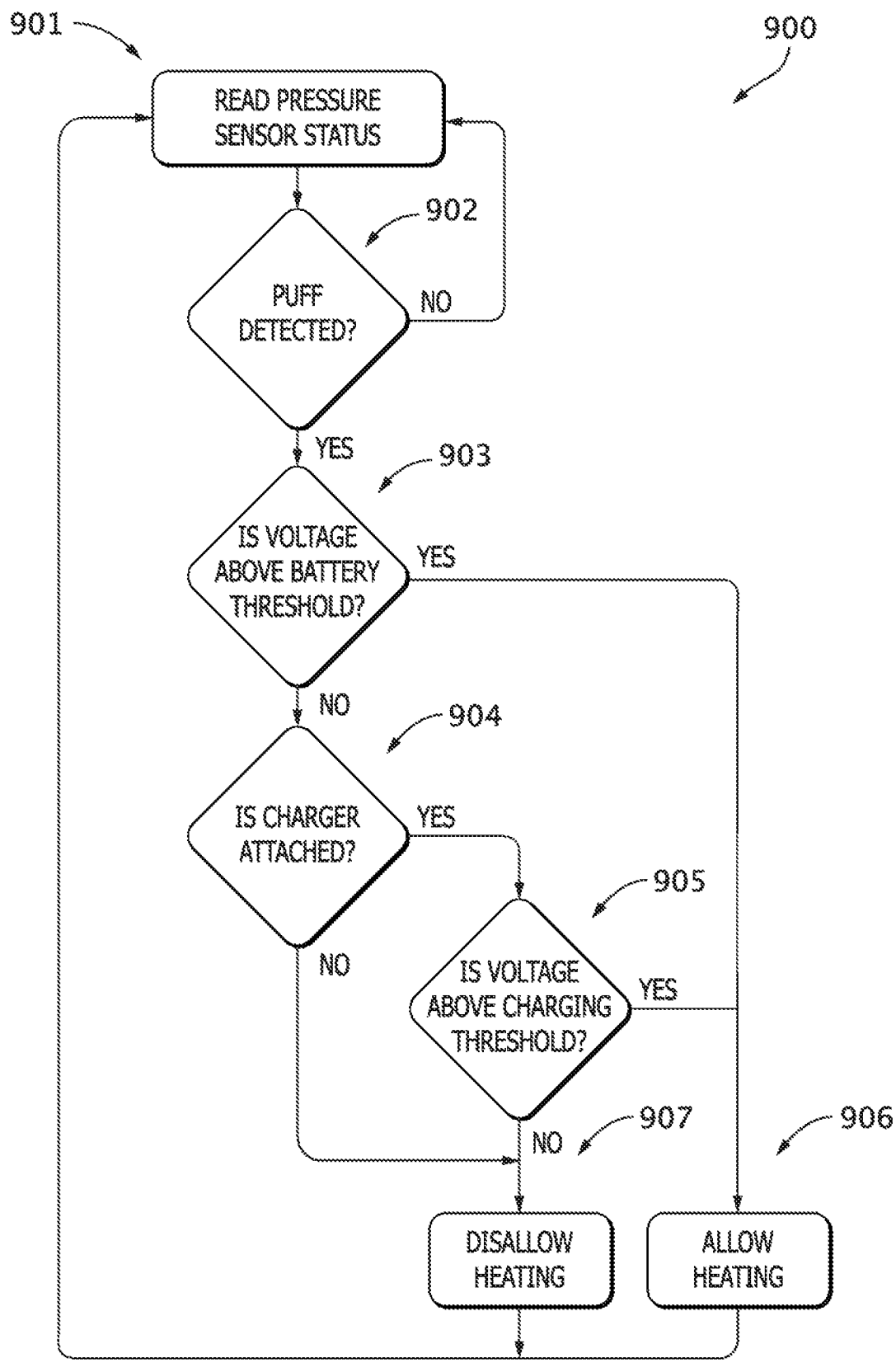

Having thus described the disclosure in the foregoing general terms, reference will now be made to the accompanying figures, which are not necessarily drawn to scale, and wherein:

FIG. 1 illustrates a control device for use in an aerosol delivery device or a vaporization system of the present disclosure according to example embodiments of the present disclosure;

FIG. 2 illustrates a partial cross-section of the control device illustrated in FIG. 1;

FIG. 3 illustrates a cartridge for use in an aerosol delivery device or a vaporization system of the present disclosure according to example embodiments of the present disclosure;

FIG. 4 illustrates a partial cross-section of the cartridge illustrated in FIG. 3;

FIGS. 5A, 5B and 5C respectively illustrate an external connector, and two chargers for use in an aerosol delivery device or a vaporization system of the present disclosure according to example embodiments of the present disclosure;

FIG. 6 illustrates components of the control device illustrated in FIG. 1 according to example embodiments of the present disclosure;

FIGS. 7(A), 7(B) and 7(C) illustrate a switch circuit in the control device illustrated in FIG. 1 according to example embodiments of the present disclosure;

FIG. 8 illustrates a flowchart showing a method of charging control according to example embodiments of the present disclosure; and FIG. 9 illustrates a flowchart showing a method of charging control according to other example embodiments of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems or vaporization systems, said terms being used herein interchangeably. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in the background art section of the present disclosure.

In one or more embodiments, the present disclosure relates to a vaporization system that includes at least elements for providing electrical power, elements for controlling output of the electrical power and additional functional capacities, and elements for forming a vapor using the electrical power. In one or more embodiments, the vaporization system can be formed of a control device and a cartridge.

An example embodiment of a control device 100 for use in an aerosol delivery device or a vaporization system of the present disclosure is shown in FIG. 1. The control device 100 comprises a device outer housing 102 that defines a device outer wall 104, a device distal end 106, and a device proximal end 108. The device proximal end 108 includes an opening 110 that provides access to a device chamber 112 that is defined by a device inner frame 114.

The nature of the control device of various embodiments is further evident in relation to FIG. 2, which shows a partial cross section of the control device 100. As seen therein, the control device 100 further includes a device battery 116 positioned within the outer housing 102 and also includes a device external connection element 118. For example, the control device 100 may have a replaceable battery or a rechargeable battery, solid-state battery, thin-film solid-state battery, rechargeable supercapacitor or the like, and thus may be combined with any type of recharging technology, including connection to a wall charger, connection to a car power source (e.g., via a cigarette lighter receptacle, USB port, etc.), and connection to a computer, such as through a universal serial bus (USB) cable or connector (e.g., USB 2.0, 3.0, 3.1, USB Type-C), connection to a USB (e.g., USB 2.0, 3.0, 3.1, USB Type-C) connector (e.g., as may be implemented in a car, wall outlet, electronic device, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, connection to an array of external cell(s) such as a power bank to charge via a USB connector or a wireless charger. An example of an inductive wireless charging system is described in U.S. Pat. App. Pub. No. 2017/0112196 to Sur et al., which is incorporated herein by reference in its entirety.

The device external connection element 118 of some embodiments is positioned at the distal end 106 of the device outer housing 102, but it will be appreciated alternative locations of the device external connection element 118 are contemplated within the scope of the disclosure. Device electrical connectors 120 are positioned in the device chamber 112 and, as illustrated, are present in sidewalls 114a of the device inner frame 114, which frame defines the boundaries of the device chamber 112. It is understood, though, that the device electrical connectors 120 may be positioned in the bottom wall 114b of the device inner frame 114. Moreover, the device electrical connectors 120 may be present at any position on the sidewalls 114a or the bottom wall 114b of the device inner frame 114. For example, the device electrical connectors 120 may be positioned at a point on the sidewalls 114a between the proximal end 108 of the device outer housing 102 and the bottom wall 114b of the device inner frame 114. Further, the device electrical connectors 120 may be positioned between a midpoint of the sidewalls 114a and the proximal end 108 of the device outer housing 102 (i.e., in an upper half of the sidewalls). Alternatively, the device electrical connectors 120 may be positioned between a midpoint of the sidewalls 114a and the bottom wall 114b of the device inner frame 114 (i.e., in a lower half of the sidewalls).

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference.

As is evident from FIG. 2, the device chamber 112 is separate from the device outer housing 102. In other words, the chamber is not merely an interior space that is defined by the outer housing. Rather, the inner frame defining the chamber exists independently and separately from the outer housing. The opening of the chamber may coincide with the opening at the proximal end of the outer housing. The inner frame thus may a completely different element that is attached to the outer housing. Alternatively, the inner frame and the outer housing may be continuously formed. In either case, however, the sidewalls forming the inner frame are present interior to and separated from the outer housing. It is understood, however, that if desired, the device chamber 112 may be expressly defined by the outer housing 102. In such embodiments, the bottom wall 114b may extend between the walls forming the outer housing 102 so as to define a bottom wall of a chamber that is defined by the bottom wall and the walls of the outer housing.

The device outer housing 102 may be formed of any suitable material, such as a metal, plastic, ceramic, glass, or the like. Preferably, the device inner frame 114 is formed of the same material as used to form the device outer housing 102; however, different materials may be used.

The presently disclosed system may comprise a single control device. Such single control device can be interchangeably connectable with a plurality of cartridges to form a plurality of different vaporization systems. For example, the control device may be interchangeably connectable with a first cartridge to form a first functioning vaporization system having a first set of characteristics, and the control device may be interchangeably connectable with a second cartridge to form a second functioning vaporization system having a second, different set of characteristics. Such vaporization can comprise two different cartridges, three different cartridges, or an even greater number of different cartridges that are all interchangeable with the first control device.

The presently disclosed system may comprise a plurality of control devices (e.g., a first control device and a second control device and optionally a third control device or an even greater number of control devices). The plurality of control devices can be interchangeably connectable with at least one cartridge to form a plurality of different vaporization systems. For example, the first control device may be interchangeably connectable with a first cartridge to form a first functioning vaporization system having a first set of characteristics, and the second control device may be interchangeably connectable with the first cartridge to form a second functioning vaporization system having a second, different set of characteristics.

An example embodiment of a cartridge 300 for use in an aerosol delivery device or a vaporization system of the present disclosure is shown in FIG. 3. The cartridge 300 comprises a tank 301 that is defined by an outer tank wall 303 that includes a proximal end 305 and a distal end 307 that is closed. As such, the tank 301 may be characterized in that the tank wall 303 is a sidewall that is continuous around the tank, and the distal end 307 defines a bottom wall. The tank is configured to contain a liquid composition for vaporization—i.e., an e-liquid or aerosol precursor composition, which may be configured as otherwise described herein. The cartridge 300 further can comprise a mouthpiece 309 that is defined by an outer mouthpiece wall 311 that includes a proximal end 313 with an exit portal 315 and a distal end 317 that is engaging the proximal end 305 of the tank 301.

The cartridge 300 is further illustrated in FIG. 4. As seen therein, the cartridge 300 further includes a heater 319 and a liquid transport element 321 that extends between the heater and a liquid 323 contained within the tank 301. The heater 319 and liquid transport element 321 may be configured as separate elements that are fluidly connected or may be configured as a combined element. Moreover, the heater 319 and the liquid transport element 321 may be formed of any construction as otherwise described herein. In various implementations, the heating member may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in proximity to, and/or in direct contact with, the liquid transport element 321. The heating assembly or the heating member may be located in the control device 100 and/or the cartridge 300. In various implementations, the liquid transport element may include components (i.e., heat conducting constituents) that are imbedded in, or otherwise part of, the liquid transport element that may serve as, or facilitate the function of, the heating assembly. Some examples of various heating members and elements are described in U.S. Pat. No. 9,078,473 to Worm et al., the disclosure of which is incorporated herein by reference in its entirety. The cartridge 300 also includes one or more electrical contacts 325 that are configured to electrically connect the heater 319 with the battery 116 in the control devices 100.

A liquid transport element 321 can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element 321 thus can be any material that contains an open pore network (i.e., a plurality of pores that are interconnected so that fluid may flow from one pore to another in a plurality of direction through the element). As further discussed herein, some embodiments of the present disclosure can particularly relate to the use of non-fibrous transport elements. As such, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some embodiments, a liquid transport element 321 can be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference. The porous monolith can form a substantially solid wick.

Various embodiments of materials configured to produce heat when electrical current is applied therethrough may be employed to form the heater 319. In some embodiments, the heater 319 can be a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further embodiments, the heater 319 can be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat.

No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater 319 in particular may be configured to be substantially flat. Such heaters are described in U.S. Pat. Pub. No. 2016/0345633 to DePiano et al., which is incorporated herein by reference.

The outer tank wall 303 can be configured to be at least partially transparent or translucent so that the liquid 323 contained therein is visible externally. As such, the entire outer tank wall 303 can be transparent or translucent. Alternatively, only a single side of the outer tank wall 303 can be transparent or translucent while the remaining portions of the outer tank wall can be substantially opaque. In further embodiments, the outer tank wall 303 can be colored. The color can be configured so that the liquid 323 within the tank 301 is still visible, or the color can be configured so that the outer tank wall 303 is substantially opaque.

In one or more embodiments, the mouthpiece 309 of the cartridge 300 can be configured for engagement with the tank 301. For example, as illustrated in FIG. 3 and FIG. 4, the distal end 317 of the mouthpiece 309 can include a rim wall 330 that is at least partially inset from the outer mouthpiece wall 330, and the rim wall can be configured to engage an interior of the proximal end 305 of the outer tank wall 303. The rim wall 330 can have a length of about 1 mm to about 20 mm, about 2 mm to about 18 mm, or about 5 mm to about 15 mm. The rim wall 330 can engage the outer tank wall 303 via a friction fit alone, or the rim wall can be substantially permanently attached to the outer tank wall, such as through welding or gluing.

In some embodiments, the mouthpiece 309 may define substantially only on open interior space through which formed vapor may combine with air to form an aerosol for output through the exit portal 315 of the mouthpiece. In one or more embodiments, the mouthpiece 309 can include one or more further interior walls that can be arranged to define one or more compartments within the mouthpiece. For example, the mouthpiece can include an interior upper wall between the proximal end and the distal end of the mouthpiece and also include an interior lower wall between the interior upper wall and the proximal end of the mouthpiece. More particularly, the mouthpiece 309 can include an interior upper wall 332 between the proximal end 313 and the distal end 317. Further, the mouthpiece 309 can include an interior lower wall 334 between the interior upper wall 332 and the distal end 317 of the mouthpiece.

Two or more walls in the mouthpiece can be configured to define a vaporization chamber within which the heater can be positioned. The outer mouthpiece wall 311, the interior upper wall 332, and the interior lower wall 334 can define a vaporization chamber 342 wherein the heater 319 is positioned. The one or more electrical contacts 325 can be positioned within the portion of the outer mouthpiece wall 311 defining the vaporization chamber 342; however, it is understood that one or more electrical leads may extend from the heater 319 to one or more electrical contacts positioned at a different portion of the outer mouthpiece wall or positioned in the outer tank wall 303. One or more walls of the mouthpiece may also include one or more openings for passage therethrough of one or more further elements of the cartridge 300 or passage of formed vapor/aerosol. For example, the interior upper wall 332 can include a vapor opening 333 through which vapor formed in the vaporization chamber 342 can pass toward the exit portal 315. The vapor opening 333 in the interior upper wall 332 can be substantially centrally located therein and can be substantially aligned with the heater 319 along a longitudinal axis of the cartridge 300. As a further example, the interior lower wall 334 can include a wick aperture 335 through which the liquid transport element 321 (e.g., a wick) can pass between the heater 319 and the liquid 323 in the tank 301. The wick aperture 335 in the interior lower wall 334 can be substantially centrally located therein and can be substantially aligned with the heater 319 along a longitudinal axis of the cartridge 300. If desired, a vaporization chamber may be defined with a lower portion of the tank 301.

Two or more walls in the mouthpiece can be configured to define a cooling chamber within which formed aerosol can be allowed to expand and/or cool before passing through the exit portal. In particular, the outer mouthpiece wall 311 and the interior upper wall 332 define a cooling chamber 344 that receives formed vapor/aerosol from the heater 319, particularly that receives vapor/aerosol from the vaporization chamber 342. As such, the formed vapor/aerosol passes from the vaporization chamber 342 through the vapor opening 333 into the cooling chamber 344.

If desired, the mouthpiece 309 can include one or more elements configured to reduce or prevent leakage of condensed liquids therefrom. For example, all or a part of the interior of the mouthpiece wall 311 and/or the interior upper wall 332 defining the cooling chamber 344 can be formed from or include an absorptive or adsorptive material configured to hold liquid. Alternatively or additionally, all or a part of the interior of the mouthpiece wall 311 and/or the interior upper wall 332 defining the cooling chamber 344 can be configured to direct liquid back toward the atomization chamber 342, such as through the addition of microchannels or the like.

In one or more embodiments, the cartridge 300 can be configured such that the mouthpiece wall 311 can include a flange positioned between the proximal end 313 and the distal end 317 thereof. For example, a flange 350 can be present and can extend circumferentially from the mouthpiece wall 311 around substantially the entirety of the mouthpiece 309. The distance that the flange 350 extends from the mouthpiece wall 311 can be substantially uniform around the entire circumference of the mouthpiece 309. In some embodiments, the distance that the flange 350 extends from the mouthpiece wall 311 can vary at one or more points around the circumference of the mouthpiece 309. The overall cartridge 300 or the mouthpiece 309 separately can be defined in relation to a longitudinal axis (L), a first transverse axis (T1) that is perpendicular to the longitudinal axis, and a second transverse axis (T2) that is perpendicular to the longitudinal axis and is perpendicular to the first transverse axis. The overall cartridge 300 and/or the mouthpiece 309 thus may be defined in relation to a total length along the longitudinal axis (L), a total width along the first transverse axis (T1), and a total depth along the second longitudinal axis (T2). The length may be greater than the width, which in turn may be greater than the depth. The distance that the flange 350 extends away from the mouthpiece wall 311 may be greater along the second transverse axis (T2) than along the first transverse axis (T1). Thus, in alternative embodiments, the total distance between opposing outer edges of the flange 350 across the mouthpiece 309 along the first transverse axis (T1) may be greater than the total distance between opposing edges of the flange across the mouthpiece along the second transverse axis (T2); the total distance between opposing outer edges of the flange 350 across the mouthpiece 309 along the first transverse axis (T1) may be substantially equal to the total distance between opposing edges of the flange across the mouthpiece along the second transverse axis (T2); or the total distance between opposing outer edges of the flange 350 across the mouthpiece 309 along the first transverse axis (T1) may be less than the total distance between opposing edges of the flange across the mouthpiece along the second transverse axis (T2). In particular embodiments, a distance (d2) between the mouthpiece wall 311 and an outer edge of the flange 350 as measured along the second transverse axis (T2) may be greater than a distance (d1) between the mouthpiece wall and an outer edge of the flange as measured along the first transverse axis (T1). Said distances (d1, d2) particularly may be as measured at about a midpoint of each of the first transverse axis (T1) and the second transverse axis (T2).

The flange 350 can interact with a corresponding lip on the control device 100 to ensure proper connection of the cartridge 300 with the control device. For example, referring to FIG. 1, the device 100 can be configured so that the opening 110 at the device proximal end 108 includes a recess with an inwardly projecting lip 121. The recess thus may comprise a rim wall 122 that is substantially parallel with the longitudinal axis of the device 100. The rim wall 122 extends downwardly from the proximal end 108 a short distance, which distance can substantially correspond to a thickness of the flange 350 of the cartridge 300 and/or the thickness of a further element that may be present adjacent the flange.

The flange 350 and/or the inwardly projecting lip 121 may be configured to bias the cartridge 300 into connection with the device 100. For example, a magnetic connection may be utilized. For example, the cartridge 300 may include a magnet 352 positioned adjacent a bottom surface of the flange 350. The magnet 352 may extend substantially completely around the circumference of the mouthpiece 309 or may be discontinuous so as be configured as one or a plurality of discrete magnets. The magnet 352 may be adhered to the mouthpiece wall 311, may be adhered to the flange 350, or may be adhered to both the mouthpiece wall and the flange. The inwardly projecting lip 121 may be formed of a metal or other material to which the magnet 352 will be attracted by magnetic force. In further embodiments, the magnet 352 may be positioned on the device 100. Specifically, the magnet 352 may be adhered to the inwardly extending lip 121. In such embodiments, the flange 350 may be formed of a metal or other material to which the magnet 352 will be attracted by magnetic force. In further embodiments, the magnet 352 may be present on the cartridge 300 as well as the device 100. If desired, the magnet 352 may be positioned at the distal end 307 of the tank wall 303 to interact with a magnetic element positioned within the device chamber 112, and particularly on the bottom wall 114b.

The device 100 can be configured in some embodiments so that at least a portion of the tank 301 is visible when the cartridge 300 is engaged with the device. As noted above, at least a portion of the outer tank wall 303 can be configured to be at least partially transparent or translucent so that the liquid 323 contained therein is visible externally. As such, the outer wall 104 of the device 100 can be configured to include a window 135 through which the outer tank wall 303 and optionally any liquid 323 present in the tank 301 can be visible when the cartridge 300 is engaged with the device 100. The window 135 may be configured as a cut-out in the outer wall 104 of the device 100 or may be configured as a notch extending from the proximal end 108 of the outer wall 104 of the device 100 a distance toward the distal end 106 of the device. Moreover, the window 135 may be completely open or the window may have a transparent member (e.g., glass or plastic) positioned in the opening defined by the window or covering the window on one or both of the inner surface and outer surface of the outer wall 104 of the device 100.

In one or more embodiments, the device 100 may include a light source 139 and at least one opening 137 through the outer wall 104 of the device through which light from the light source is visible. The light source 139 may comprise, for example, one or more light emitting diodes (LED) capable of providing one or more colors of lighting. The light source 139 can be positioned directly on the printed circuit board (PCB) 141 on which further control components (e.g., a microcontroller and/or memory components) may be included. The opening 137 may be provided in any desired shape and may particularly be positioned near the distal end 106 of the device 100. The opening 137 may be completely open or may be filled, such as with a light guide material, or may be covered with a transparent or translucent member (e.g., glass or plastic) on one or both of the inner surface and the outer surface of the outer wall 104 of the device 100. The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

An airflow sensor, pressure sensor, or the like may be included in the device. For example, as shown in FIG. 2, the device 100 can include a sensor 143 on the PCB 141. Configurations of a printed circuit board and a pressure sensor, for example, are described in U.S. Pat. Pub. No. 2015/0245658 to Worm et al., the disclosure of which is incorporated herein by reference. The sensor 143 can be positioned anywhere within the device 100 so as to subject to airflow and/or a pressure change that can signal a draw on the device and thus cause the battery 116 to delivery power to the heater 319 in the cartridge 300. Alternatively, in the absence of an airflow sensor, the heater 319 may be activated manually, such as by a push button. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

An input element may be included with the aerosol delivery device (and may replace or supplement an airflow or pressure sensor). The input may be included to allow a user to control functions of the device and/or for output of information to a user. Any component or combination of components may be utilized as an input for controlling the function of the device 100. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. As still a further example, a capacitive sensor may be implemented on the aerosol delivery device to enable a user to provide input, such as by touching a surface of the device on which the capacitive sensor is implemented. In another example, a sensor capable of detecting a motion associated with the device (e.g., accelerometer, gyroscope, photoelectric proximity sensor, etc.) may be implemented on the aerosol delivery device to enable a user to provide input. Examples of suitable sensors are described in U.S. Pat. App. Pub. No. 2018/0132528 to Sur et al., and U.S. Pat. App. Pub. No. 2016/0158782 to Henry et al., which are incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator. Likewise, a flow sensor may be replaced with a manual actuator, such as a push button.

FIG. 5A illustrates an external connector for use in an aerosol delivery device or a vaporization system of the present disclosure according to some example embodiments of the present disclosure. It will be appreciated that the external connector illustrated in FIG. 5A is provided by way of example, and not by way of limitation. In this regard, aerosol delivery devices in accordance with various embodiments may be used in conjunction with a variety of external connectors having different shapes and form factors and/or mating interfaces. For example, depending upon the shape/form factor of the aerosol delivery device, any corresponding mating interface implemented on the aerosol delivery device (e.g., such as the well 106a ), the type and/or location of device external connection element 118 available on the aerosol delivery device, and/or other factors may be utilized. In one or more embodiments, the vaporization system formed by any combination of one or more device(s) and one or more cartridge(s) can further include an external connector 500 configured for electrical contact with the device external connection element 118. The external connector 500 can include a first connector end 503 and a second connector end 505 interconnected by a union 507, which may be, for example, a cord of variable length. The first connector end 503 can be configured for electrical and, optionally, mechanical connection with the device 100. In particular, the first connector end 503 can include an inset wall 503a that can be received within a well (e.g., well 106a at the distal end 106 of the device 100) present at the distal end 106 of the device 100. The external connector 500 can include a plurality of electrical pins 511 interior to the inset wall 503a configured for making a charging and/or information transferring connection with the device external connection element 118. In some embodiments, the device 100 can include a mechanical connector 119 adjacent the device external connection element 118. The mechanical connector 119 can be a magnet or a metal (or like element) that is adapted for magnetic attraction to a magnet. The first connector end 503 then can likewise include a mechanical connection element 513 that is positioned between the inset wall 503a and the electrical pins 511. The mechanical connection element 513 can be a magnet or a metal (or like element) that is adapted for magnetic attraction to a magnet. The second connector end 505 can be configured for connection to a computer or similar electronic device or for connection to a power source. As illustrated, the second connector end 505 has a Universal Serial Bus (USB) connection; however, a different connection may also be provided and/or an adapter may likewise be included (e.g., a USB/AC adapter). For example, an adaptor including a USB connector at one end and a power unit connector at an opposing end is disclosed in U.S. Pat. Pub. No. 2014/0261495 to Novak et al., which is incorporated herein by reference.

FIG. 5B illustrates a charger 518 for use in an aerosol delivery device or a vaporization system of the present disclosure according to some example embodiments of the present disclosure. As sown in FIG.5B, the charger 518 may include a charger base 520, contacts 521 and a connector end 522 with a USB connection. The charger 518 may be connected to the power supply using USB cable 523. FIG. 5C illustrates a charger 530 for use in an aerosol delivery device or a vaporization system of the present disclosure according to some example embodiments of the present disclosure. The charger 530 may include a charger base 531 and contacts 532. The charger 530 can be connected to the power supply using cable 533. In some embodiments, the charger base 518 and/or 530 can be made by metal (e.g., Aluminum) or plastic materials.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 1 ml or more, about 2 ml or more, about 5 ml or more, or about 10 ml or more of the aerosol precursor composition may be included.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

FIG. 6 illustrates components of the control device 100 illustrated in FIG. 1 according to example embodiments of the present disclosure. As shown, the control device 100 includes a rechargeable battery 601. In some examples, the rechargeable battery 601 may correspond to the battery 116 illustrated in FIG. 2. The control device 100 also includes an electrical connector 602 such as a USB charging connector that is configured to interconnect the rechargeable battery 601 with a suitable power supply. In some examples, the electrical connector 602 may correspond to the external connector 500, or more specifically the first connector end 503 illustrated in FIG. 5A. In some embodiments, the electrical connector 602 can connect to the rechargeable battery 601 via USB charging circuit 603. The electrical connector 602 and the charging circuit 603 are included in charging circuitry of the control device 100. The electrical connector 602 can connect to the power supply via a charger 604. In some examples, the charger 604 may include a wall transformer or a USB charging source or other source as otherwise described herein. In some embodiments, the control device 100 may include multiple rechargeable batteries 601.

In some embodiments, the control device 100 can detect that the charger 604 is connected and begin charging the rechargeable battery 601. When the electrical connector 602 is connected to the power supply via the charger 604, if a user attempts to draw puffs, the rechargeable battery 601 may be isolated from the power supply. To achieve this, in some embodiments, the control device 100 includes a sensor 605 configured to detect an action of using the aerosol delivery device by a user and output a signal indicating detection of the action, which can be a puff action by the user. The control device 100 also includes a microprocessor 606 coupled to the charging circuitry including the USB charging circuit 603 and coupled to the sensor 605.

In some embodiments, the microprocessor 606, in response to receiving the signal from the sensor 605, is configured to determine a state of the aerosol delivery device indicating an occurrence of a passage of electrical current from the power supply to the rechargeable battery 601 through the electrical connector 602. The microprocessor 606 of some embodiments is configured, in response to the determination, to discontinue the passage of the electrical current from the power supply to the rechargeable battery 601 through the electrical connector 602. In some such embodiments, the microprocessor 606 is configured to discontinue the passage of the electrical current using a switch circuit 607 between the electrical connector 602 and the rechargeable battery 601. For example, the switch circuit 607 can be opened to disconnect the electrical connector 602 from the USB charging circuit 603 and thereby from the rechargeable battery 601.

In some embodiments, after the current from the power supply to the rechargeable battery 601 is discontinued, the microprocessor 606 is configured to activate the aerosol delivery device. The aerosol delivery device is activated so that power is delivered from the rechargeable battery 601 to a further element of the aerosol delivery device to provide an output in response to the action of using the aerosol delivery device by the user while the electrical connector 602 is connected to the power supply. In some embodiments, the further element includes a heating element configured to heat and thereby vaporize components of an aerosol precursor composition contained within a housing of the aerosol delivery device. As such, the output in response to the action of using the aerosol delivery device may be formation of an aerosol for inhalation by the user. For example, the further element may correspond to the heater 319 illustrated in FIG. 4. Thus, the action of using the device can be puffing on the device, and the output in response to the puff on the device can be formation of an aerosol for inhalation. In some embodiments, the aerosol precursor composition is a liquid, or a solid or semi-solid. In further embodiments, the further element may correspond to another functional component of the device, such as a feedback element (e.g., a vibrating component or a lighting component or a sound component) that is configured to provide a status of the device. In this manner, powering of the aerosol delivery device during use of the device (e.g., while forming aerosol and/or while making other use of the device) comes directly from the battery and not from the power supply to which the electrical connector 602 is connected. In some embodiments, the microprocessor 606 may be configured to activate the aerosol delivery device simultaneously when the current from the power supply to the rechargeable battery 601 is discontinued. In some embodiments, the microprocessor 606 may be configured to activate the aerosol delivery device or initiate the activation of the aerosol delivery device before current from the power supply to the rechargeable battery 601 is discontinued.

An output in response to an action of using the aerosol delivery device can be any activity by the device that requires delivery of power from the battery to a further element of the aerosol delivery device. As noted above, the output may be the formation of aerosol due to delivery of power from the battery to a heater that vaporizes a liquid aerosol precursor composition. In some embodiments, the output may be activation of a status indicator (e.g., a light, a haptic element, a sound element, a display, etc.) to provide an indication of a status of the device in response to an action of using the device, such as shaking of the device or touching a capacitive sensor on the device. In such embodiments, a sensor may include a device (such as a gyroscope or similar element) that is configured to sense movement of the device.

In some embodiments, the above operations may be implemented by the microprocessor 606. For example, instructions of the above operations may be stored as computer-readable program codes in a non-transitory memory. The microprocessor 606 can be configured to execute the computer-readable program codes to implement the instructions of the above operations. The microprocessor 606 may be a number of processors, a multi-core processor or some other type of processor, depending on the particular implementation. Further, the microprocessor 606 may be implemented using a number of heterogeneous processor systems in which a main processor is present with one or more secondary processors on a single chip. As another illustrative example, the microprocessor 606 may be a symmetric multi-processor system containing multiple processors of the same type. In yet another example, the microprocessor 606 may be embodied as or otherwise include one or more ASICs, FPGAs or the like. Thus, although the microprocessor 606 may be capable of executing a computer program to perform one or more functions, the microprocessor 606 of various examples may be capable of performing one or more functions without the aid of a computer program. In either instance, the microprocessor 606 may be appropriately programmed to perform functions or operations according to example implementations of the present disclosure.

In some embodiments, since there is no current from the power supply to the rechargeable battery 601, the heating element is only powered by the remaining power in the rechargeable battery 601, not by the power supply. In this way, the control device 100 allows vaping by a user while the aerosol delivery device or more specifically the electrical connector 602 is connected to the charger 604.

FIGS. 7(A)-7(C) illustrate the switch circuit 607 in the control device 100 illustrated in FIG. 1 according to example embodiments of the present disclosure. As shown in FIG. 7(A), in one embodiment, the switch circuit 607 includes a pair of metal-oxide-semiconductor field-effect transistor (MOSFET) switches respectively coupled to a positive electrical connection and a negative electrical connection of the electrical connector 102. The microprocessor 606 of this embodiment is configured to disconnect both the positive and negative electrical connections from the rechargeable battery 601 using the switch circuit 607. For example, microprocessor 606 can control to open both the MOSFET switches.

As shown in FIG. 7(B), in another embodiment, the switch circuit 607 includes a pair of opto-isolator relays respectively coupled to a positive electrical connection and a negative electrical connection of the electrical connector 102. The microprocessor 606 of this embodiment is configured to disconnect both the positive and negative electrical connections from the rechargeable battery 601 using the switch circuit 607. For example, microprocessor 606 can control to open both the opto-isolator relays.

As shown in FIG. 7(C), in another embodiment, the switch circuit 607 includes a MOSFET switch integrated with the charging circuitry 603 and another switch external to the charging circuitry 603. The microprocessor 606 of this embodiment is configured to disconnect the electrical connector 602 from the rechargeable battery 601 using the switch circuit 607. For example, the external switch can send an enable signal to the microprocessor 606, the microprocessor 606 can control to open the MOSFET switch integrated with the charging circuitry 603 and open the external switch based on the enable signal.

In a further example, the switch circuit 607 is coupled to one or both of a positive electrical connection and a negative electrical connection of the electrical connector 602. The microprocessor of this example is configured to disconnect only one of the positive and negative electrical connections from the rechargeable battery 601 using the switch circuit 607.

In some embodiments, after the current from the power supply to the rechargeable battery 601 is discontinued, the sensor 605 can detect that the use has finished the action such as the puff action. In response to detecting a completion of the action by the sensor 605, the microprocessor 606 of such embodiments is configured to determine that the electrical connector 602 is still connected to the power supply although there is no current from the power supply to the rechargeable battery 601. The microprocessor 606 is configured to reconnect the electrical connector 602 to the rechargeable battery 601 and thereby reconnect the power supply to the rechargeable battery 601 to charge the rechargeable battery 601. For example, the microprocessor 606 can control to close the switch circuit 607 such that there is a passage of electrical current from the power supply to the rechargeable battery 601 through the electrical connector 602.

FIG. 8 illustrates a flowchart showing a method 800 of charging control according to example embodiments of the present disclosure. As shown, in such embodiments, at block 801, the microprocessor 606 can read pressure sensor status of the sensor 605. At block 802, the microprocessor 606 of such embodiments can determine whether a puff action by the user is detected by the sensor 605 based on the output signal from the sensor 605. If no puff action is detected, the method 800 can go back to block 801 so that the microprocessor 606 can continue to monitor the sensor status. On the other hand, if a puff action is detected, the method 800 can proceed to block 803.

At block 803, the microprocessor 606 of such embodiments can determine if charging is enabled. Charging is enabled if the microprocessor 606 can determine an a state of the aerosol delivery device indicating occurrence of a passage of electrical current from the power supply to the rechargeable battery 601 through the electrical connector 602. If charging is enabled, the microprocessor 606 of such embodiments can disable charging connections to discontinue the passage of the electrical current from the power supply to the rechargeable battery 601 through the electrical connector 602, as explained above. After the passage of the electrical current is discontinued, the microprocessor 606 can control to activate vapor mechanism such as the heater 319 to allow puffing, as shown at block 805. On the other hand, if charging is not enabled, the microprocessor 606 of such embodiments can directly activate the vapor forming mechanism, as shown at block 805.

The microprocessor 606 of such embodiments can continue to monitor the sensor status to read pressure sensor status and determines whether the user has finished the puff action, as shown at blocks 806 and 807 respectively. If the puff action is completed, the microprocessor 606 of such embodiments can determine whether the electrical connector 602 is still connected to the power supply although there is no current from the power supply to the rechargeable battery 601, as shown at block 808. If the charge source is still present, i.e., the electrical connector 602 is still connected to the power supply, the microprocessor 606 of such embodiments can reconnect the electrical connector 602 to the rechargeable battery 601 and thereby reconnect the power supply to the rechargeable battery 601 to charge the rechargeable battery 601, as shown at block 809.

A typical low-battery threshold for a 3.7V e-cigarette battery can be about 3.4V. This low-battery threshold can vary between 3.3V to 3.5V depending on the rest of the circuits and the vapor/heating mechanism. At this threshold, there is ample power for the microprocessor 606 to continue operating, lighting LED's, etc. However, high-amperage heating is inhibited in order to protect the battery cell from over-discharge. In one example, the battery threshold when normally operating on the rechargeable battery 601 alone is set to 3.5V. If the voltage of the rechargeable battery 601 is lower than 3.5V, the user is not able to activate the heater 319 and a low battery indication is given via LED or other method. If the user establishes a charging connection between the aerosol delivery device and a charging device (e.g., the charger 604) at this point, the rechargeable battery 601 may take an unacceptably long time to absorb enough charge current to rise above the 3.5V threshold and cause the microprocessor 606 to resume allowance of puff activity.

In some instances, it would be desirable to allow puffs to occur as soon as the aerosol delivery device (with depleted battery) is connected to the charger, even though the battery level is still below the low-battery threshold. Allowing puffs to occur as soon as the aerosol delivery device (with depleted battery) is connected to the charger can be achieved by having a different puff prevention voltage threshold (e.g., a lower threshold) when operating on the rechargeable battery 601 while connected with the charger 604 than the single threshold that may be used when operating on the rechargeable battery 601 alone.

In some embodiments, when the charger 604 is connected to the electrical connector 602, the microprocessor 606 can lower the low-battery threshold from 3.5V (e.g., to a voltage in the range of about 3.4V or about 3.3V) in order to allow the user to activate the heater while the electrical connector 602 is connected to the power supply. Other different voltage thresholds, both prior to charging and with the charger connected can be used in other embodiments. In some embodiments, depending on a particular battery manufacturer's charge and discharge curves such as curves appropriate for particular battery chemistry, cell capacity, etc., age or number of recharge cycles of the battery, the microprocessor and heating circuitry, and/or the desired user experience, values of the voltage thresholds can be characterized and tuned to any combination of voltages.

In some embodiments, the control device 100 may include a rechargeable battery 601 and a supplemental energy storage element such as a supercapacitor or a supplemental battery. The supplemental energy storage element can provide power to the heating element to produce an aerosol that is sufficient for a predetermined number of puffs, e.g., 10 puffs, or a predetermined time period, e.g., 5 minutes. In such embodiments, if the rechargeable battery 601 can provide sufficient power to the heating element to produce an aerosol to the user for puffing, the supplemental energy storage element may not be used to provide power to the heating element. When the rechargeable battery 601 is connected to the charger 604 for charging, the microprocessor 601 may check the supplemental energy storage element. If the supplemental energy storage element can provide power to the heating element to produce an aerosol that is sufficient for a predetermined number of puffs or a predetermined time period, the microprocessor 606 can control the charger 604 to start charging the rechargeable battery 601. If during the charging, an action of the user, e.g., a puff action, is detected, and the rechargeable battery 601 has not recovered enough capacity to provide sufficient power to the heating element, the microprocessor 606 can activate the supplemental energy storage element to provide power to the heating element to produce an aerosol that is sufficient for a predetermined number of puffs or a predetermined time period. The power provided by the supplemental energy storage element may depend on the recovery time of the rechargeable battery 601. The recovery time may be the time that the rechargeable battery 601 needs to be charged to provide sufficient power to the heating element to produce an aerosol to the user for puffing. In such embodiments, the rechargeable battery 601 and the supplemental energy storage element may have isolated connections to the heating element. Thus, when power from the supplemental energy storage element is being provided to the heating element, the rechargeable battery 601 can be charged simultaneously.

FIG. 9 illustrates a flowchart showing a method 900 of charging control according to other examples embodiment of the present disclosure. As shown, in such embodiments, at block 901, the microprocessor 606 can read pressure sensor status of the sensor 605. At block 902, the microprocessor 606 of such embodiments can determine whether a puff action by the user is detected by the sensor 605 based on the output signal from the sensor 605. If no puff action is detected, the method 900 can go back to block 901 so that the microprocessor 606 can continue to monitor the sensor status. On the other hand, if a puff action is detected, the method 900 can proceed to block 903.

At block 903, the microprocessor 606 of such embodiments can determine if voltage of the rechargeable battery 601 is higher than the battery threshold when operating on the rechargeable battery 601 alone such as 3.5V. If the voltage of the rechargeable battery 601 is higher than the battery threshold, the method 900 can go directly to block 906 where the microprocessor 606 can allow the activation of the heater 319 in the aerosol delivery device to carry out the puff action. On the other hand, if the voltage of the rechargeable battery 601 is lower than the battery threshold, the method 900 can go to block 904.

At block 904, the microprocessor 606 of such embodiments can determine if the electrical connector 602 is connected to the power supply via the charger 604. If not, the method 900 can go to block 907. Since the voltage of the rechargeable battery 601 is lower than the battery threshold and there is no charger connected to charge the rechargeable battery 601, the rechargeable battery 601 can be at low-battery level and the microprocessor 606 of such embodiments can disallow the activation of the heater 319 in the aerosol delivery device to carry out the puff action, as shown at block 907.

On the other hand, if at block 904, the microprocessor 606 of such embodiments can determine that the electrical connector 602 is connected to the power supply via the charger 604, the microprocessor 606 can alter the voltage threshold of the rechargeable battery 601 from a higher value to a lower value such as from about 3.5V to about 3.3 V. The lower value may be referred to as a charging threshold when operating on the rechargeable battery 601 with the charger 604 connected, which is lower than the battery threshold as described above. The method 900 can go from block 904 to block 905.

At block 905, the microprocessor 606 of such embodiments can perform a comparison between the voltage of the rechargeable battery 601 and the charging threshold of the rechargeable battery 601 (e.g., about 3.3V) to determine whether the voltage of the rechargeable battery 601 is higher than the charging threshold. If the voltage of the rechargeable battery 601 is higher than the charging threshold (but still lower than the battery threshold of about 3.5V), the microprocessor 606 of such embodiments can allow the activation of the heater 319 in the aerosol delivery device to carry out the puff action, as shown at block 906. On the other hand, if the voltage of the rechargeable battery 601 is lower than the charging threshold, the microprocessor 606 can disallow the activation of the heater 319 in the aerosol delivery device to carry out the puff action, as shown at block 907.

The methods 800 and 900 can be used together or separately. For example, if the microprocessor 606 determines a state of the aerosol delivery device indicating an occurrence of a passage of electrical current from the power supply to the rechargeable battery 601 through the electrical connector 602, the microprocessor 606 can open the switch circuit 607 to discontinue the passage of the electrical current and alter the voltage threshold of the rechargeable battery 601 from the higher value to the lower value to allow puffs to occur. In another example, when the microprocessor 606 detects the puff action and determines that the electrical connector 602 is connected to the power supply (the switch circuit 607 can be opened or closed), the microprocessor 606 can alter the voltage threshold of the rechargeable battery 601 from the higher value to the lower value to allow puffs to occur in response to connection of the aerosol delivery device to the charger 604.

Many modifications and other embodiments of the disclosure will come to mind to one skilled in the art to which this disclosure pertains having the benefit of the teachings presented in the foregoing descriptions and the associated figures. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
a rechargeable battery;
charging circuitry including an electrical connector configured to interconnect the rechargeable battery with a power supply;
a sensor configured to detect an action of using the aerosol delivery device by a user and output a signal; and
a microprocessor operatively coupled with the charging circuitry and the sensor, the microprocessor, in response to receiving the signal from the sensor, being configured to:
determine a state indicating a passage of electrical current from the power supply to the rechargeable battery through the electrical connector;
in response to the state indicating the passage of electrical current from the power supply to the rechargeable battery:
determine an output voltage of the rechargeable battery, and compare the output voltage of the rechargeable battery to a first low-battery threshold and a second low-battery threshold, the second low-battery threshold being less than the first low-battery threshold;
in response to the action of using the aerosol delivery device by the user and the output voltage of the rechargeable battery being less than the first low-battery threshold but greater than the second low-battery threshold, activate the aerosol delivery device so that power is delivered from the rechargeable battery to a further element of the aerosol delivery device to provide the output; and in response to the output voltage of the rechargeable battery being less than the second low-battery threshold, deactivate the aerosol delivery device so that power is not delivered from the rechargeable battery to the further element.

2. The aerosol delivery device of claim 1, wherein the microprocessor is further configured to discontinue the passage of the electrical current using a switch circuit between the electrical connector and the rechargeable battery.

3. The aerosol delivery device of claim 2, wherein the switch circuit includes a pair of metal-oxide-semiconductor field-effect transistor (MOSFET) switches respectively coupled to a positive electrical connection and a negative electrical connection of the electrical connector, and the microprocessor being configured to discontinue the passage of the electrical current includes being configured to disconnect both the positive and negative electrical connections from the rechargeable battery using the switch circuit.

4. The aerosol delivery device of claim 2, wherein the switch circuit includes a pair of opto-isolator relays respectively coupled to a positive electrical connection and a negative electrical connection of the electrical connector, and the microprocessor being configured to discontinue the passage of the electrical current includes being configured to disconnect both the positive and negative electrical connections from the rechargeable battery using the switch circuit.

5. The aerosol delivery device of claim 2, wherein the switch circuit is coupled to one or both of a positive electrical connection and a negative electrical connection of the electrical connector, and the microprocessor being configured to discontinue the passage of the electrical current includes being configured to disconnect only one of the positive and negative electrical connections from the rechargeable battery using the switch circuit.

6. The aerosol delivery device of claim 2, wherein the switch circuit includes a MOSFET switch integrated with the charging circuitry and another switch external to the charging circuitry, and the microprocessor being configured to discontinue the passage of the electrical current includes being configured to disconnect the electrical connector from the rechargeable battery using the switch circuit.

7. The aerosol delivery device of claim 2,
wherein the microprocessor being configured to discontinue the passage of the electrical current includes being configured to disconnect either or both of a positive electronical connection of the electrical connector to the rechargeable battery and a negative electrical connection of the electrical connector to the rechargeable battery using the switch circuit; and
wherein the microprocessor being configured to cause the flow of electrical current from the power supply to the rechargeable battery includes being configured to reconnect either or both of the positive electrical connection and the negative electrical connection of the electrical connector to the rechargeable battery and thereby reconnect the power supply to the rechargeable battery to charge the rechargeable battery.

8. The aerosol delivery device of claim 1, wherein the action includes a puff action by the user.

9. The aerosol delivery device of claim 1, wherein the further element includes a heating element configured to heat and thereby vaporize components of an aerosol precursor composition contained within a housing of the aerosol delivery device such that the output in response to the action of using the aerosol delivery device is formation of an aerosol.

10. The aerosol delivery device of claim 9, wherein the aerosol precursor composition contained is a liquid, solid or semi-solid.

11. The aerosol delivery device of claim 1, wherein, in response to the state indicating no passage of electrical current from the power supply to the rechargeable battery, the microprocessor is further configured to:
determine a second output voltage of the rechargeable battery, and compare the second output voltage of the rechargeable battery to the first low-battery threshold; and
in response to the action of using the aerosol delivery device by the user and the second output voltage of the rechargeable battery being greater than the first low-battery threshold, activate the aerosol delivery device so that power is delivered from the rechargeable battery to a further element of the aerosol delivery device to provide an output.

12. The aerosol delivery device of claim 11, wherein, in response to the second output voltage of the rechargeable battery being less than the first low-battery threshold, the microprocessor is configured to deactivate the aerosol delivery device so that power is not delivered from the rechargeable battery to the further element.

13. The aerosol delivery device of claim 1, wherein the microprocessor is further configured to cause the passage of the electrical current from the power supply to the rechargeable battery and to discontinue the passage of the electrical current from the power supply to the rechargeable battery.

* * * * *